US005484941A

United States Patent [19]
Kaestner et al.

[11] Patent Number: 5,484,941
[45] Date of Patent: Jan. 16, 1996

[54] PREPARATION OF 3(5)-METHYLPYRAZOLES

[75] Inventors: Ralf Kaestner; Stefan Rittinger; Peter Paessler, all of Ludwigshafen; Norbert Rieber, Mannheim, all of Germany

[73] Assignee: BASF Aktiengesellschaft, Ludwigshafen, Germany

[21] Appl. No.: 232,291

[22] PCT Filed: Nov. 3, 1992

[86] PCT No.: PCT/EP92/02514

§ 371 Date: May 6, 1994

§ 102(e) Date: May 6, 1994

[87] PCT Pub. No.: WO93/10098

PCT Pub. Date: May 27, 1993

[30] Foreign Application Priority Data

Nov. 11, 1991 [DE] Germany .......................... 41 37 011.2

[51] Int. Cl.$^6$ ................................................. C07D 231/12
[52] U.S. Cl. ..................................... 548/373.1; 548/377.1
[58] Field of Search ............................................ 548/373.1

[56] References Cited

U.S. PATENT DOCUMENTS

| 2,900,044 | 8/1959 | Scofield . |
| 2,941,020 | 6/1960 | Dunn . |
| 3,235,557 | 6/1967 | Scharein et al. . |
| 3,706,181 | 12/1972 | Walker et al. . |

FOREIGN PATENT DOCUMENTS

| 274600 | of 0000 | European Pat. Off. . |
| 748193 | of 0000 | France . |
| 2157537 | of 0000 | Germany . |
| 1222910 | of 0000 | Germany . |

OTHER PUBLICATIONS

Journal of Organic Chemistry, Bd. 34, No. 4, Apr. 1969.
Chem. Abstracts, vol. 94, 1981, Abst. No. 174287e.

Primary Examiner—Robert W. Ramsuer
Attorney, Agent, or Firm—Keil & Weinkauf

[57] ABSTRACT

Process for the preparation of methylpyrazoles from diacetylene and hydrazines in which the diacetylene is removed from cracked gas by absorption and is then reacted with hydrazines.

9 Claims, No Drawings

PREPARATION OF 3(5)-METHYLPYRAZOLES

This application is a 371 Pct/Ep 92/02514 filed Nov. 3, 1992.

The present invention relates to a process for the preparation of 3(5)-methlpyrazoles from diacetylene and hydrazine.

3-Methylpyrazole and its derivatives are important nitrification inhibitors for ammoniacal fertilizers (cf U.S. Pat. No. 4,975.107 and DE 2,745,633 A1, for example).

N-Substituted pyrazoles are of industrial significance as components of numerous biologically active agents (cf, e.g., EP 286,969-A; EP 320,750; EP 234,045-B1; EP 0,269,806-B1).

Methods of synthesizing 3(5)-methylpyrazole from diacetylene and hydrazine on a laboratory scale are known (Schroth et al, Z. Chem. 9, (1969), 110; Paudler et al, J. Org. Chem., 34, (1969), 999).

Disclosures in the literature indicate that diacetylene is extremely difficult to handle in large-scale operations (cf, e.g., DE-AS 1,222,910), for which reason this compound is virtually only used for small-scale syntheses in the laboratory (EP 274,600 A1).

Zh. Prik. Khim. 44 (1971), 1921 also discloses the reaction of diacetylene with hydrazine hydrate. This reference recommends the purification of pyrolysis gases (cracked gas) by means of this reaction, and this gives rise to the following problems: The cracked gas generally has a content of unsaturated hydrocarbons having three or more carbon atoms of only 0.5% or less. This makes the cracked gas hardly suitable as a source of diacetylene for synthesis reactions due to the fact that the low concentration of diacetylene would necessitate the reaction of very large quantities of gas. Moreover, the cracked gas, not having undergone any purification and thus containing higher acetylenes in undue proportions, would yield numerous by-products.

DE-OS 2,157,537 proposes a way of avoiding such problems by the employment of a method of safely handling low molecular-weight acetylenes which consists of adsorbing such acetylenes on to activated charcoal and subjecting them to subsequent processing operations in this form. This method is extremely complicated, and a continuous process poses engineering problems on account of the adsorptive agent.

EP 274,600 reveals a process for the reaction of diacetylene with alcohols, which is reportedly capable of being carried out on an industrial scale by the addition of certain higher hydrocarbons.

It is an object of the present invention to provide a process for the preparation of 3(5)-methylpyrazoles of the formulae Ia and Ib

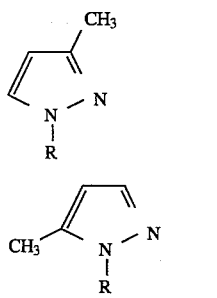

in which R denotes hydrogen, a $C_1$–$C_6$ alkyl radical or an optionally substituted phenyl radical, in which diacetylene can be reacted with hydrazines in a simple manner without incurring engineering problems.

We have now found that this object can be achieved by
(a) separating, by absorption, a diacetylene-containing partial stream from the cracked gas resulting from the acetylene synthesis,
(b) reacting this partial stream with hydrazines of the formula II

in which R has the meaning stated above.

Surprisingly, the partial gas stream containing the higher acetylenes as obtained in the normal industrial process for working up cracked gas can be directly reacted with hydrazine to give very good yields of 3(5)-methylpyrazoles without the need for physical or chemical pretreatment of said gas stream. The yields are, unexpectedly, much higher than those stated in the literature for reactions with pure diacetylene (cf Paudler and Schroth loc. cit., 73% and 80% respectively).

The reaction can be illustrated by the following scheme:

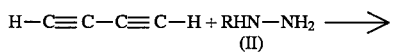

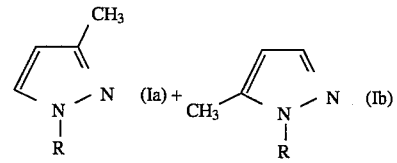

where R denotes hydrogen, $C_1$–$C_6$ alkyl or an optionally substituted phenyl radical. The compounds of the formulae Ia and Ib are together referred to as 3(5)-methylpyrazoles.

The various industrial processes used for the production and purification of the cracked gas used in the process of the invention are well known (cf Ullmanns Encyclopedia of Industrial Chemistry, 5th Edition, A1, 1985, 97 et seq, 111, FIG. 13), for which reason they are only briefly outlined here:

Hydrocarbons (e.g. natural gas or, possibly, higher-boiling fractions) are cracked at the high temperatures required for the production of acetylene, and the resulting gases are rapidly cooled by injected quench water or quench oil immediately on leaving the reaction zone. The composition of the cracked gas depends on the materials subjected to the cracking process and on the cracking conditions used.

The partial streams used in the process of the invention occur as a number of partial streams produced when the cracked gas is separated by a number of physical operations (preferably by absorption followed by desorption in a series of washing and stripping circuits). It is characteristic of the useful partial streams containing higher acetylenes that they contain diacetylene in much higher concentrations than the cracked gas (ie, they are diacetylene-enriched).

Preferably, the partial streams used in the process of the invention contain a diluent, or a diluent is added to said partial streams. The diluent can be liquid or gaseous.

Suitable diluents are, in general, polar liquids, e.g., organic solvents such as alcohols, especially methanol, ketones, N-methylpyrrolidone, and/or dimethyl formamide. If desired, water can be used in admixture with said polar liquids. Other suitable diluents are mixtures of higher-boiling hydrocarbons, benzene, toluene, or xylenes.

The liquid diluent can be the absorbent used in process step a).

The radical R is preferably hydrogen, that is to say, it is preferred to use unsubstituted hydrazine. The resulting methylpyrazoles of the general formulae Ia and Ib in which R denotes hydrogen form a tautomeric system, ie, they convert to each other at room temperature.

R may also denote a $C_1$–$C_6$ alkyl radical or an optionally substituted phenyl radical. Possible substituents on the phenyl radical are a variety of radicals such as hydroxy, halo (especially fluoro), cyano, nitro, $C_1$–$C_4$ alkyl, $C_1$–$C_4$ haloalkyl, ($C_1$–$C_6$ alkoxy)($C_1$–$C_4$ alkyl), $C_1$–$C_6$ alkoxy), ($C_1$–$C_6$ alkoxy)($C_1$–$C_4$ alkoxy), $C_1$–$C_6$ haloalkoxy, $C_1$–$C_4$ alkylthio, $C_1$–$C_4$ haloalkylthio, carboxy, ($C_1$–$C_4$ alkoxy)carbonyl, $C_1$–$C_4$ alkylsulfonyl, $C_1$–$C_4$ haloalkylsulfonyl, $C_1$–$C_4$ alkylsulfonyl, $C_1$–$C_4$ haloalkylsulfonyl, $C_1$–$C_4$ alkysulfonyloxy, halo($C_1$–$C_4$ alkyl)sulfonyloxy, phenyl, halophenyl, phenoxy, and halophenoxy.

The process of the invention makes it possible to handle diacetylene and react it with hydrazines on an industrial scale without the risk of explosion. This is of particular advantage in those processes in which the partial streams containing higher acetylenes coming from the cracking process would otherwise have to be burned or, purely for the sake of disposal, recycled to the cracking process (cf Ullmann, loc. cit.).

Both liquid partial streams and gaseous partial streams, obtained by stripping (desorption) of the washings, are characterized by a more favorable distribution profile of the higher acetylenes, as compared with the initial cracked gas, for the desired purpose of conversion to methylpyrazoles. Only insignificant amounts of other higher acetylenes (pentadiene, hexadiene, etc.) are present, since these are removed at an earlier stage. This leads to a high degree of purity of the methylpyrazoles obtained.

The separation of the diacetylene-containing partial stream from the cracked gas is carried out, preferably, by causing the higher acetylenes to be absorbed by a liquid employed for a first wash of the cracked gas containing all of the acetylene. The resulting diacetylene-enriched washings may then be degasified in a vacuum stripper, and the vapors are stabilized by dilution with an inert gas prior to or immediately after compression thereof, if carried out.

The diacetylene-containing hydrocarbon mixtures ("BTX fractions") obtained from this gas stream by condensation are equally suitable for the conversion of diacetylene to methylpyrazoles as described above. This procedure has an additional advantage, since these BTX condensates cannot normally serve any useful industrial purpose apart from incineration, on account of their diacetylene content. Once the diacetylene has been converted to methylpyrazoles, the first overhead fraction is diacetylene-free BTX, which can be used as a starting point for, say, the manufacture of benzene.

The preferred absorbents used for working up the cracked gas are high-boiling hydrocarbons or polar liquids, for example N-alkyllactams having $C_1$–$C_3$ alkyl moieties, especially N-methylpyrrolidone, $C_1$–$C_5$ alcohols, especially $C_3OH$, acid amides, especially dimethylformamide, alkylated cyclic ureas, especially dimethylpropylene urea, water, $C_1$–$C_6$ amines, or $NH_3$.

A typical liquid partial stream containing higher acetylenes has the following composition: benzene 32%, toluene 28%, xylene (BTX) 17%, styrene 8%, diacetylene 6%. Another example of the composition of a partial stream is as follows: MeOH 89%, acetylene 0.6%, diacetylene 2.2%, vinylacetylene 0.4%, cyclopentadiene 1%, benzene 1.8%, and toluene 1.3%.

The diacetylene-containing gas removed from the absorbent can be diluted with, advantageously, natural gas, but other inert gases are also suitable, for example hydrocarbons, CO, synthesis gas, lean gas, $N_2$, or mixtures of said gases.

The gas mixture which has thus been rendered inert as regards spontaneous decomposition of the diacetylene, preferably contains from 55 to 85 vol % of inert gas, from 1 to 30 vol % of diacetylene, and from 10 to 20 vol % of other constituents such as acetylene, vinyl acetylene, and benzene. The concentration of diacetylene in the inertisized gas mixture is preferably from 5 to 20 vol %. The upper limit is governed by the limit of spontaneous explosive decomposition in the inert gas. A typical gas mixture has the following composition: 58% of $CH_4$, 18% of diacetylene, 5% of nitrogen, 4% of acetylene, 4.5% of vinyl acetylene, 4% of benzene, 2% of $C_2H_6$, 2% of cyclopentadiene, and 2.5% of residual constituents.

The preferred procedure for carrying out the reversible absorption of the diacetylene to effect its separation is as follows: The cracked gas containing all of the acetylene is prewashed with the polar liquid acting as absorbent, the absorbent is degassed in a vacuum stripper, absorbent still present in the gas stream is then washed out with water, and the diacetylene-containing gas is cooled.

The reaction temperature used to carry out the reaction between the diacetylene and hydrazines is advantageously from −40° to 150° C., temperatures between 50° and 120° C. being particularly suitable for achieving good yields with almost quantitative diacetylene conversion.

The reaction can be carried out at slightly reduced or elevated pressure, but higher compression is not advisable for safety reasons. The best results are attained at atmospheric pressure.

The reaction of the partial stream with the hydrazines or solutions thereof can be carried out as a batch process or, alternatively, as a continuous process with parallel flow or countercurrent flow of the streams. If a gaseous partial stream is used, it is advantageous to use a process known to achieve good distribution of gases in liquids, for example those making use of facilities such as liquid/gas-mixing rings, perforated trays, or spray reactor/absorber towers.

The gas mixture leaving the acetylene production usually has an operating temperature which is slightly above ambient temperature. Separation, at ambient temperature, of readily condensable constituents of the gas in separators disposed upstream of the reactor improves the purity of the crude product.

The hydrazines are advantageously used in pure form or as an aqueous solution of hydrazine. However, it is also possible to use a solution of hydrazine in some other proton-transferring solvent or in a polar aprotic solvent such as an alcohol, acid amide, lactam, or alkylated urea, as mentioned above with respect to suitable polar liquids, or an ester, lactone, or glycol ether, especially ethylene glycol diethyl ether, or less polar solvents such as ethers, aromatics, and hydrocarbons.

The reaction step (b) of the process of the invention is preferably carried out by recycling the unconverted portions of hydrazines to the reaction, a procedure which presents no engineering problems.

In the following examples, the inertisized diacetylene-containing gas mixture is designated as HA gas and the diacetylene as DA. The diacetylene-containing absorbate from the first wash of the cracked gas is referred to as the prewashings (with naming of the solvent). The diacetylene-containing solution from the bottom of the HA gas condenser is abbreviated to BTX solution. The diacetylene content of the HA gas and the off-gas following the reaction was determined gaschromatographically on a packed column (20% Reoplex 400 on Chromosorb PAW) using nitrogen as carrier gas (35 mL/min) and a flame ionization detector. The concentrations are given in percentages by volume.

Example I

HA gas is passed at a rate of 100 L/h through a glass frit (D2) at the base of a bubble-cap column having a capacity of 2 L and filled with 1,000 g of hydrazine hydrate 64 wt % of hydrazine) heated at 100° C.

This HA gas had been obtained by subjecting cracked gas from an acetylene production plant to a multistage purifying process in which the higher acetylenes were extracted by washing the cracked gas with a little N-methylpyrrolidone stripped gas with cooling water (recovery of the NMP) and cooling it to about 20° to 40° C. (separation of high-boiling portions). The diacetylene concentration had then been adjusted to from 14 to 18 vol % by metering in natural gas (before and after compression to about 1.3 bar). Finally, the HA gas had been tempered to an operating temperature of about 40° C. in a water-cooled separator.

At an average diacetylene depletion of more than 90%, 88% of the hydrazine was converted over a period of 18 h. Purification was effected by distillation (possible at atmospheric pressure or in vacuo) to give 1,290 g of 3-methylpyrazole (3-MP) having a purity of >99.4%; yield 90% based on converted hydrazine.

EXAMPLE 2

110 g of 25% hydrazine hydrate were circulated through a trickle column at 60° C. HA gas (obtained as described in Example 1) was passed through countercurrently at a rate of 10 L/h, the DA content of said HA gas varying from 4 to 13%. After a reaction time of 20 h, 3-MP had formed at a selectivity of 95% (GC analysis of the crude effluent), the conversion of hydrazine being 20%.

EXAMPLE 3

In the manner described in Example 1,100 g of 64% hydrazine hydrate were reacted with HA gas at 80° C. and a gas flow rate of 50 L/h. The DA content fluctuated between 5 and 12%. After a reaction temperature of 40 h, the hydrazine conversion was 85%. Distillation yielded 126 of 3-MP; yield 90% based on hydrazine converted.

EXAMPLE 4

2,500 S of 64% hydrazine hydrate were reacted with HA gas in a 5 L bubble-cap column at 60° C. The HA had a diacetylene content of from 8 to 13% and was metered at a rate of from 150 to 180 L/h. The average DA depletion over 35 h was 92%. Fractional distillation permitted the recovery of 650 g of unconverted hydrazine in aqueous solution. There were obtained 2,050 g of 3-MP having a purity 99.5%; yield 84% based on hydrazine converted.

EXAMPLE 5

Using the apparatus described in Example 4, 2,000 g of hydrazine hydrate were mixed with HA gas at 80 until the conversion of the hydrazine was complete. The DA content of the HA gas fluctuated between 6 and 15%. The gas in-flow rate was 150 L/h and the DA depletion up to a hydrazine conversion of 88% was more than 85%. After 80 h, 99.4% of the hydrazine used as starting material had undergone conversion. Fractional distillation yielded 7 g of hydrazine (in aqueous solution) and 3,009 g of 3-MP; yield 91.8% based on hydrazine converted.

EXAMPLE 6

Using the apparatus described in Example 1, HA gas was passed through 1,000 g of 64% hydrazine hydrate at a rate of 80 L/h at 60° C. The DA concentration of the in-flowing gas fluctuated between 12 and 14%. The average DA depletion of the HA gas was 70%, and after 30 h 80% of the hydrazine had undergone conversion. Fractional distillation yielded 127 g of hydrazine (in aqueous solution) and 1,248 g of 3-MP; yield 95% based on hydrazine converted.

EXAMPLE 7

Using the apparatus described in Example 1, HA gas was passed through 1,000 g of 64% hydrazine hydrate at a rate of 100 L/h at room temperature (20° C.). The reaction heated up spontaneously to 37° C. The DA concentration of the in-flowing gas fluctuated between 12 and 19%. Over 35 h, 70% of the hydrazine converted at an average DA depletion of 75%. Fractional distillation of the crude effluent yielded 1,024 g of 3-MP having a purity of 99.6%; yield 89.3% based on hydrazine converted.

EXAMPLE 8

HA gas was passed through 2,000 of 64% hydrazine hydrate at a rate of 120 L/h. The DA content of the in-flowing gas fluctuated between 11 and 17%. Following an operating period of 30 h, 82% of the hydrazine used as starting material had undergone conversion. The fractional distillation yielded 234 (18%) of unconverted hydrazine as an aqueous solution containing 35% of 3-methylpyrazole (198). 2,295 of 3(5)-methylpyrazol distilled off; purity >99%. The total yield of 3(5)-methylpyrazole from these two streams was thus 92.9% based on hydrazine converted.

The stream containing hydrazine (565 g) was replenished with 64% hydrazine hydrate to a weight of 1,000 g (total hydrazine content 41.4%). HA gas (DA content 13 to 16.5%) was passed through at a rate of 120 L/h at 80° C. for 15 hours, after which 83% of the hydrazine had undergone conversion. There were isolated, by fractional distillation, 1,251 g of 3(5)-methylpyrazole; yield 97% based on hydrazine converted.

EXAMPLE 9

471 of BTX solution having a DA content of 5.6% were placed in a stirred vessel equipped with a reflux condenser, and 50 g of $N2H_4$. $H_2$ were added thereto. The mixture was stirred and heated to a gentle boil. No diacetylene could be detected after a period of one hour, at which point the 3-methylpyrazole content was 7.5%, this corresponding to a yield of approximately 85%. Fractional distillation yielded a first fraction at a temperature of from 80° to 100° C. at atmospheric pressure consisting of a mixture of BTX aromatics and water. Phase separation of the condensate gave 420 g of diacetylene-free BTX.

EXAMPLE 10

Using the equipment described in Example 1,100 L/h of HA gas were passed through a mixture of 500 g of hydrazine hydrate and 500 of dimethylformamide (DMF) at 60° C. The initial concentration of the DA varied between 12 and 19%.

The average depletion of of the DA from the HA gas was more than 85%. Fractional distillation yielded 610 g of pure 3-MP (yield 93%, based on hydrazine converted).

EXAMPLE 11

In a stirred vessel having a capacity of 100 mL and equipped with a reflux condenser there were added 5 g (0.1 mol) Of hydrazine hydrate to 50 of a 2.2% strength solution of diacetylene in MeOH, corresponding to cracked gas prewashings, at 60° C. After a period of 2 hours no diacetylene could be detected, and 3-methylpyrazole had formed at a selectivity of 82%, based on the hydrazine used.

EXAMPLE 12

Using equipment as described in Example 11, 50 g of said methanolic prewash solution were added to 5 g of hydrazine hydrate at 80° C. On completion of the addition, the mixture was refluxed for a further 2 hours at 70° C. The diacetylene was quantitatively converted, forming 3-methylpyrazole at a selectivity of 81% based on hydrazine used.

EXAMPLE 13

250 L/h of HA gas were passed up through absorber equipment having a diameter of 40 and a height of 320 ram and loosely packed with 3 mm glass Raschig rings, the gas entering via a perforated glass tray and having a diacetylene content which fluctuated between 6.6% and 14.8%. A stream of liquid was circulated at a rate of 52 L/h countercurrently to the gas stream, the initial concentration of the liquid stream being 64% of $N_2H_2 \cdot H_2O$. The circulated liquid showed a depletion of hydrazine from 64% to about 15%, over which range there was obtained a space-time yield of 3-MP of 123 g/L.h.

EXAMPLE 14

In a bubble-cap column (diameter 2 mm) equipped with a gas inlet frit of glass (pore diameter 40–90 μm, D2), there was placed a mixture of 90 g of methyl hydrazine and 60 g of $H_2O$, which was heated to 80° C. A partial stream of HA off-gas coming from an acetylene production plant was bubbled through the reaction solution for 18 hours at a rate of 20 L/h. The diacetylene concentration of the HA gas at the reactor inlet fluctuated between 11 and 15%. At an average depletion of diacetylene of more than 80% there were obtained 127 g (66% yield) of 1,5-dimethylpyrazole and 35 g (18% yield) of 1,3-dimethylpyrazole.

EXAMPLE 15

In a stirred vessel having a capacity of 500 mL and equipped with a reflux condenser there was placed a solution of 18.8 g of phenylhydrazine in 50 g of N-methylpyrrolidone, which was heated to 60° C. A total of 100 mL of HA-containing prewashings (diacetylene content approx. 8.5% in NMP) from the cracked gas processing portion of an acetylene production plant over a period of 24 h. The solution became visibly darker in color and contained, at the end of the reaction, 12% of the two isomers 1-phenyl-3(5)-methylpyrazoles (yield ca 80%).

We claim:
1. A process for the preparation of a methylpyazole of the formula Ia or Ib

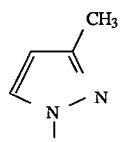
(Ia)

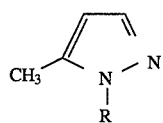
(Ib)

in which R denotes hydrogen, a $C_1$–$C_6$-alkyl radical or an optionally substituted phenyl radical, from diacetylene and a hydrazine, comprising
(a) separating, by reversible absorption in a polar liquid, a diacetylene-containing partial stream from the cracked gas coming from an acetylene synthesis plant and diluting the partial stream with an inert gas,
(b) reacting this partial stream, without intermediate physical or chemical treatment, with a hydrazine of the formula II

 RHN—$NH_2$ (II), in which R has the meaning stated above, at temperatures ranging from –40° to +150° C. under standard pressure.

2. A process as defined in claim 1, wherein the absorbent used in process step a) is water, an alcohol, a ketone, benzene, toluene, xylene, dimethylformamide, N-methylpyrrolidone, or a mixture thereof.

3. A process as defined in claim 1, wherein the inert gas used is a low-boiling hydrocarbon mixture, hydrogen, carbon monoxide, nitrogen, natural gas, acetylene, or a mixture of said gases.

4. A process as defined in claim 1, wherein the polar liquid used is N-methylpyrrolidone.

5. A process as defined in claim 1, wherein the inert gas used is natural gas.

6. A process as defined in claim 1, wherein the content of diacetylene following dilution with inert gas is from 5 to 30 vol %.

7. A process as defined in claim 1, wherein the hydrazine is used as pure substance, in the form of an aqueous solution or in the form of a solution in a proton-donating or aprotic solvent.

8. A process as defined in claim 1, wherein unconverted hydrazine is recycled to the reaction.

9. A process as defined in claim 1, wherein the reversible absorption of the diacetylene of process step (a) is effected by prewashing the cracked gas containing all of the acetylene with the polar liquid, degassing the absorbent in a vacuum stripper, washing out the absorbent still present in the gas stream with water, and cooling the diacetylene-containing gas.

* * * * *